United States Patent
Li

(10) Patent No.: US 9,590,433 B2
(45) Date of Patent: Mar. 7, 2017

(54) TERMINAL AND ELECTRONIC WATER-RESISTANCE METHOD

(71) Applicant: ZTE CORPORATION, Shenzhen, Guangdong Province (CN)

(72) Inventor: Xiaotang Li, Shenzhen (CN)

(73) Assignee: ZTE Corporation (CN)

( * ) Notice: Subject to any disclaimer, the term of this patent is extended or adjusted under 35 U.S.C. 154(b) by 0 days.

(21) Appl. No.: 15/028,324

(22) PCT Filed: Jun. 9, 2014

(86) PCT No.: PCT/CN2014/079468
§ 371 (c)(1),
(2) Date: Apr. 8, 2016

(87) PCT Pub. No.: WO2014/180428
PCT Pub. Date: Nov. 13, 2014

(65) Prior Publication Data
US 2016/0241059 A1    Aug. 18, 2016

(30) Foreign Application Priority Data
Oct. 9, 2013  (CN) .......................... 2013 1 0466865

(51) Int. Cl.
*G06F 1/16* (2006.01)
*H02J 7/00* (2006.01)
(Continued)

(52) U.S. Cl.
CPC ........ *H02J 7/0031* (2013.01); *G01N 21/1717* (2013.01); *G01N 21/552* (2013.01);
(Continued)

(58) Field of Classification Search
CPC .............................. G06F 1/16; B63C 2011/023
(Continued)

(56) References Cited

U.S. PATENT DOCUMENTS

2012/0055838 A1*  3/2012  Shinoda ................. H04M 1/18
                                                             206/525
2013/0088094 A1   4/2013  Paik
(Continued)

FOREIGN PATENT DOCUMENTS

CN         2745259 Y     12/2005
CN       202309804 U      7/2012
(Continued)

OTHER PUBLICATIONS

International Search Report and Written Opinion issued Sep. 12, 2014 in PCT Patent Application No. PCT/CN2014/079468.
(Continued)

*Primary Examiner* — John J Lee
(74) *Attorney, Agent, or Firm* — Plumsea Law Group, LLC

(57) ABSTRACT

A terminal and electrical water-resistance method, the terminal includes: a circuit board, a battery providing a power source for the circuit board, a housing provided with a transparent medium used for reflecting light; the circuit board includes: a detection module, configured to: emit light towards the transparent medium, receive the light reflected by the transparent medium to convert into electric signal data to send to a control module; the control module, configured to: receive the electric signal data to compare with preset data, trigger the power-off switch when a difference value between the electric signal data and the preset data reaches a preset threshold which is preset according to the light and the transparent medium, wherein, the preset data are electric signal data when the light is totally reflected by the transparent medium; a power-off switch configured to: disconnect a connection between the circuit board and the battery after triggering.

17 Claims, 2 Drawing Sheets

Light is emitted towards a transparent medium, light reflected by the transparent medium is received, and the received reflection light is converted into electric signal data  — 11

The electric signal data is compared with preset data, and a connection between a circuit board and a battery is disconnected when a difference value between the electric signal data and the preset data reaches a preset threshold  — 12

(51) Int. Cl.
*H04M 1/18* (2006.01)
*G01N 21/17* (2006.01)
*H04B 1/3827* (2015.01)
*H04M 1/02* (2006.01)
*G01N 21/552* (2014.01)
*H04B 1/38* (2015.01)
*G01N 21/55* (2014.01)
*H01M 10/42* (2006.01)

(52) U.S. Cl.
CPC .......... *H04B 1/3833* (2013.01); *H04M 1/026* (2013.01); *H04M 1/18* (2013.01); *G01N 2021/1723* (2013.01); *G01N 2021/555* (2013.01); *G06F 1/16* (2013.01); *H01M 2010/4271* (2013.01); *H04B 2001/3894* (2013.01)

(58) Field of Classification Search
USPC ............... 455/575.1, 550.1, 551, 575.8, 90.3
See application file for complete search history.

(56) References Cited

U.S. PATENT DOCUMENTS

| | | | |
|---|---|---|---|
| 2013/0220841 A1* | 8/2013 | Yang | A45C 11/00 206/37 |
| 2013/0335898 A1* | 12/2013 | Stevens | H05K 13/00 361/679.01 |
| 2014/0262847 A1* | 9/2014 | Yang | A45C 11/00 206/37 |

FOREIGN PATENT DOCUMENTS

| | | |
|---|---|---|
| JP | 5251602 B2 | 7/2013 |
| KR | 20110022106 A | 3/2011 |
| WO | 2005123470 A1 | 12/2005 |

OTHER PUBLICATIONS

European Search Report issued Sep. 29, 2016 for EP Application No. 14794888.9.

* cited by examiner

TERMINAL AND ELECTRONIC WATER-RESISTANCE METHOD

CROSS-REFERENCE TO RELATED APPLICATION(S)

This application is the U.S. National Phase application of PCT application number PCT/CN2014/079468 having a PCT filing date of Jun. 9, 2014, which claims priority of Chinese patent application 201310466865.2 filed on Oct. 9, 2013, the disclosures of which are hereby incorporated by reference.

TECHNICAL FIELD

The present document relates to the electrical water-resistance field, and in particular, to a terminal and an electrical water-resistance method in the electrical water-resistance field.

BACKGROUND OF RELATED ART

With the increasing popularity of the mobile phone usage, the situations of the water damage of the mobile phone are more and more; especially for the mobile phone with the built-in battery, due to being unable to timely remove the battery, it is much more easy to appear the water damage of the circuit board of the mobile phone, while the water damage of the circuit board is usually difficult to be repaired, which only can be replaced with a high cost and low customer satisfaction.

At present, in the electrical water-resistance field, the disadvantage of the related art is that: a water triggering circuit is arranged in the housing, and a relay switch circuit is always in a power-on state after the triggering, the water triggering circuit is failed when the user erases the water on the housing surface, and then the connection between the power supply and the mobile phone circuit is recovered, while the failure of the water-resistance function is caused due to the water inside the machine; or, a field effect transistor, a bistable circuit and a reset circuit are added on the circuit board of the mobile telephone, while those circuits and the field effect transistor are easy to appear short circuit failure after the water goes inside the mobile phone, which cannot block the battery output and cannot do anything about the water-resistance function; or, it is required that the protection circuit is triggered only when the positive and negative electrode output ends of the battery and the water induction end are waterlogged at the same time; while the output terminal of the battery is not the first waterlogging point when being used for the mobile phone, therefore, the working circuit of the mobile phone will be caused to burn due to the short circuit by water and the protection circuit is still not triggered; when the mobile phone is waterlogged at several locations inside itself, the user installs the battery again after removing the water on the battery output end, and it still will be burned due to the short circuit by water on the mobile phone working circuit, that is, the water-resistance function failure will be appeared after the disassembly of the battery; or, a humidity sensor is located in the housing, the power-off is triggered with a requirement of multiple locations with water inside the machine, which cannot break the power at the moment when the housing of the mobile phone contacts the water, and there is a security risk; in addition, because the control processing circuits, such as, the controller, the memory, etc., are always in a power-on state, the circuits are easy to fail when the machine is waterlogged inside itself.

SUMMARY

The technical problem to be solved by the embodiment of the present document is to provide a terminal and an electrical water-resistance method, which can automatically disconnect the power supply of the circuit board to protect the circuit board from water damage when the water immersion is detected.

In order to solve the above technical problem, the following technical scheme is adopted:

the embodiment of the present document provides a terminal, including: a circuit board, a battery and a housing, wherein the battery provides a power source for the circuit board, the housing is provided with a transparent medium used for reflecting light, and the circuit board comprises: a detection module, a control module and a power-off switch, wherein, the detection module is configured to: emit light towards the transparent medium, receive the light reflected by the transparent medium, and convert the light into electric signal data and send the electric signal data to the control module;

the control module is configured to: after receiving the electric signal data, compare the electric signal data with preset data and trigger the power-off switch when a difference value between the electric signal data and the preset data reaches a preset threshold, wherein, the preset data are electric signal data when the light is totally reflected by the transparent medium, and the preset threshold is preset according to the light and the transparent medium; and the power-off switch is configured to: after being triggered, disconnect a connection between the circuit board and the battery.

Alternatively, the above terminal further has the following characteristics:

the power-off switch is further configured to: after being triggered, connect to a positive electrode and a negative electrode of the battery.

Alternatively, the above terminal further has the following characteristics:

the control module is configured to trigger the power-off switch through the following mode: sending a command of supplying power for the power-off switch to the power-off switch when the difference value between the electric signal data and the preset data reaches the preset threshold.

Alternatively, the above terminal further has the following characteristics: the terminal further comprises: a power supply module, wherein, the power supply module is configured to: supply power for the power-off switch after receiving the command of supplying power for the power-off switch; and the power-off switch is configured to: after receiving power supply, disconnect the connection between the circuit board and the battery.

Alternatively, the above terminal further has the following characteristics:

the power-off switch comprises: an electromagnet and a switch button connected with a switch shrapnel, the switch shrapnel is connected with the circuit board and the battery;

the power supply module is configured to: supply power for the electromagnet after receiving the command of supplying power for the power-off switch; and the electromagnet is configured to: adsorb the switch shrapnel after being supplied with power, enable the switch shrapnel to disconnect the connection between the circuit board and the battery, and connect to the positive electrode and the negative electrode of the battery.

Alternatively, the above terminal further has the following characteristics:

a refractive index of the transparent medium is larger than a refractive index of water; and the transparent medium comprises any of the following mediums: glass, resin, plastic, precious stone and quartz.

In order to solve the above problem, the embodiment of the present document further provides an electrical water-resistance method applied to the above terminal, including:

emitting light towards a transparent medium set in a housing, and receiving light reflected by the transparent medium, and converting the light into electric signal data; and comparing the electric signal data with preset data, and disconnecting a connection between a circuit board and a battery when a difference value between the electric signal data and the preset data reaches a preset threshold, wherein, the preset data are electric signal data when the light is totally reflected by the transparent medium, and the preset threshold is preset according to the light and the transparent medium.

Alternatively, the above method further has the following characteristics: after disconnecting the connection between the circuit board and the battery, it further comprises:

connecting to a positive electrode and a negative electrode of the battery.

Alternatively, the above method further has the following characteristics: the step of disconnecting a connection between a circuit board and a battery comprises:

supplying power for a power-off switch, and the power-off switch disconnecting the connection between the circuit board and the battery after receiving power supply.

Alternatively, the above method further has the following characteristics:

the power-off switch comprises: an electromagnet and a switch button connected with a switch shrapnel, wherein, the switch shrapnel is connected with the circuit board and the battery;

the step of the power-off switch disconnecting the connection between the circuit board and the battery after receiving power supply comprises:

the electromagnet adsorbing the switch shrapnel after being supplied with power, enabling the switch shrapnel to disconnect the connection between the circuit board and the battery, and connecting to the positive electrode and the negative electrode of the battery.

In sum, the embodiment of the present document provides a terminal and an electrical water-resistance method, which uses more reliable power-off switch circuit and is able to disconnect the battery output in time when the mobile phone and other terminal products using the lithium battery accidentally fall into the water or are thrown by liquid, to avoid the water damage of the circuit board.

PREFERRED EMBODIMENTS

The embodiments of the present document are described in detail with reference to the accompanying drawings hereinafter. It should be illustrated that, in the case of not conflicting, the embodiments and features of these embodiments in the present application can be arbitrarily combined with each other.

Figure 1:
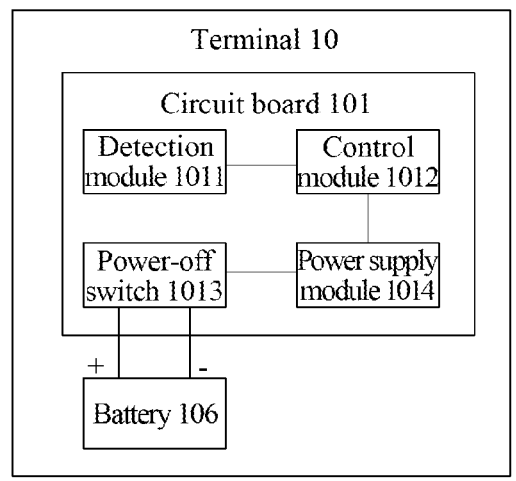
FIG. 1 is a schematic diagram of a terminal of an embodiment of the present document.
Figure 2:
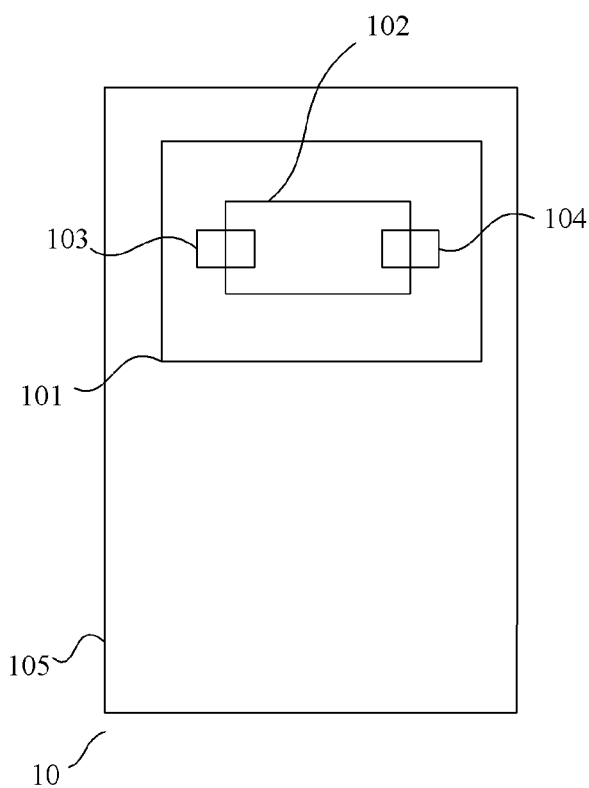
FIG. 2 is a plane block diagram of a terminal of an embodiment of the present document.

As shown in FIGS. 1 and 2, a terminal 10 of the present embodiment includes a circuit board 101, a battery 106, a housing 105, the battery 106 provides power for the circuit board 101, the housing 105 is provided with a transparent medium 102 used for reflecting light, and the circuit board 101 is provided with a detection module, a control module and a power-off switch, wherein, the detection module 1011 is configured to: emit light towards the transparent medium 102, and receive the light reflected by the transparent medium 102, convert the light into electric signal data and send the electric signal data to the control module;

the control module 1012 is configured to: after receiving the electric signal data, compare the electric signal data with preset data and trigger the power-off switch when a difference value between the electric signal data and the preset data reaches a preset threshold, wherein, the preset data are electric signal data when the light is totally reflected by the transparent medium, and the preset threshold is preset according to the light and the transparent medium;

the power-off switch 1013 is configured to: after being triggered, disconnect a connection between the circuit board 101 and the battery 106.

Wherein, the power-off switch is further configured to: after being triggered, connect to a positive electrode and a negative electrode of the battery. The short circuit of the positive electrode and the negative electrode can start a protective measures inside the battery, to disconnect the battery, and there is no output at the battery; in this case, even if the water goes into the switch which causes the connection between the circuit board and the battery, because the battery is in a short circuit protection state without any output, there will not be a power-on damage failure of the mobile phone circuit.

In an alternative embodiment, the control module is configured to trigger the power-off switch through the following mode: sending a command of supplying power for the power-off switch to the power-off switch when the difference value between the electric signal data and the preset data reaches the preset threshold.

The power supply module 1014 is configured to: supply power for the power-off switch after receiving the command of supplying power for the power-off switch; and the power-off switch 1013 is configured to: after receiving the power supply, disconnect a connection between the circuit board and the battery.

In an alternative embodiment, the power-off switch 1013 can include: an electromagnet and a switch button connected with a switch shrapnel, the switch shrapnel is connected with the circuit board and the battery;

the power supply module 1014 is configured to: supply power for the electromagnet after receiving the command of supplying power for the power-off switch;

the electromagnet is configured to: adsorb the switch shrapnel after being supplied with power, enable the switch shrapnel to disconnect the connection between the circuit board and the battery, and connect to the positive electrode and the negative electrode of the battery.

Wherein, the detection module 1011 can be composed of a LED light emitter 103 and a photoelectric receiving tube 104. The transparent light reflecting medium is arranged on the housing 105, and the refractive index of the medium is larger than that of the water.

The LED emits the light, an appropriate incident angle is selected which is greater than a total reflection critical angle at a boundary of the medium and the air, and enables the emission light to be totally reflected by the reflecting medium; the reflected light is received by the photoelectric receiving tube, converted to the electric signal data and sent to the control module; and the electric signal data are stored in the memory, as the preset data.

When there is water or other liquid covering the reflecting medium, because the refractive index of the water or other liquid is larger than that of air, the total reflection critical angle is increased; the designed incident angle is less than the critical angle at the moment, and then there is a part of the light refracted by the water or other liquid, of which the reflected light is reduced; and the reflected light is received by the photoelectric receiving tube, converted into the electric signal data and sent to the control module.

The control module acquires the electric signal data from the memory when the emitted light is totally reflected, this is, the preset data, and calculates the difference value at present between the electrical signal data and the preset data; when the difference value between the two reaches a preset threshold, it means that the outer surface of the transparent medium has already covered by water or other liquid, that is, it is believed that the mobile phone falls into the water or some foreign liquid contacts the mobile phone, and it is required to trigger the power-off switch; at that time, the control module controls the power-off switch to act and enable the battery output to be disconnected with the circuit of the terminal (such as a mobile phone) or the lithium battery to enter an overcurrent protection status without any output, to avoid the circuit board damage due to water inside the machine.

The threshold for triggering the power-off switch is preset according to different light and different mediums. For example, when water or other liquid is covering the transparent reflecting medium, because the refractive index of the water or other liquid is larger than that of air, the total reflection critical angle is increased; a part of the light is refracted by the water or other liquid, its reflected light is reduced, the current value of the reflected light obtained after the photoelectric conversion is reduced, which has a certain difference value (for different transparent mediums, the difference values are different) with the above preset data. In actual use, the refractive index of the soup and other liquid are larger than that of water, then the difference values will be different and the preset thresholds are also different; the preset threshold needs to be adjusted according to the different light and different mediums; usually, the preset threshold is set in a range of greater than 0 and less than or equal to the difference value, that is, 0<the preset threshold≤the difference value.

The power-off switch can use the electromagnet principle, and the electromagnet is supplied with power by the terminal working circuit when being triggered, and the power supply of the terminal circuit is disconnected after triggering; the power-off switch without the power supply will not be recovered by itself and will need to manually recover, to avoid the switch circuit failure due to the water inside the machine and the water-resistance function failure.

Compared with the related art, the terminal of the embodiment of the present document has the following beneficial effects:

by adopting the infrared detection technology, there is no need to set a number of water triggered switches or humidity sensors; the switch is triggered to disconnect the power supply of the terminal instantly when the mobile phone contacts the water, and the detection method is much more safe and effective; after the power-off switch is triggered, the switch circuit has no power supply instantly and is not influenced by the water inside of the machine, to avoid the failure of the power-off control circuit which is always power-on and easy to be influenced by the inside water in the related art; the power-off switch needs manual recovery after being triggered, which avoids the water-resistance function failure caused by removing the disconnection state of the power supply after the battery is removed or the visible water on the surface of the mobile phone is cleared in the related art.

The terminal of the present document is described in detail according to a specific embodiment hereinafter.

As shown in FIG. 2, an LED infrared emitter 103 and a photodiode 104 are located on the circuit board 101, at the back side of the mobile phone, and the housing 105 is provided with a reflective glass sheet.

The working principle of the infrared ray detecting the water-contact circuit is as follows: the infrared light emitted by the LED is reflected by the glass and received by the photodiode; in normal condition, the reflective glass is in contact with the air, and the infrared light enters the air through the glass, part of the infrared light is refracted by the air and part is reflected by the glass; when the incident angle between the infrared light and the glass is greater than 42 degrees, all the infrared light will be reflected by the glass without any refracted light into the air; when the mobile phone drops into the water, the reflective glass contacts the water, and the infrared light enters the water through the glass; the refractive index of water is larger than that of air, and correspondingly, only when the incident angle of the infrared light is required to be greater than 63 degrees, it can be realized to be totally reflected by the glass without any refracted light into the water; therefore, the incident angle of the infrared light is designed between 42 degrees and 63 degrees; in normal situation, the infrared light is totally reflected to the photodiode 104 by the glass and is converted to the electrical signal data, the electric signal data are used as the preset data, while when the mobile phone drops into the water and the reflective glass is covered with water, a part of the infrared light will be refracted by water, and the other part is reflected to the photodiode 104 by the glass and is converted to the electric signal data; the difference value between the electric signal data at that time and the preset data is calculated through the control module; when the difference value between the two reaches the preset threshold, it is determined that the mobile phone falls into the water, and the power control module outputs the power to the power-off switch, to enable the switch to act and disconnect the power supply of the terminal circuit board.

The threshold value is preset according to different light and different mediums, the glass with an appropriate light transmittance (such as, 89%) is selected, and the glass has a boundary with the water. When the incident angle is 45 degrees, the reflection index is about 70%, it is converted to a current value through the phototube, and the value is about 70% of the total reflection, that is, the difference value of the current value and the preset data is 30% of the total reflection. Considering that the mobile phone may fall into the other liquid (such as soup, sauce etc.), of which the refractive index is greater than that of normal water, the infrared reflectivity will be slightly higher than 70%, that is, the difference value is less than 30% of the data when the light is totally reflected. At the same time, in order to avoid the false detection when the tiny water droplets are adhered to the glass, the threshold cannot be set as too sensitive and the threshold is set as 15% of the data when the light is totally reflected, that is, the switch action command is triggered when the infrared detection module detects that the infrared reflection signal is lower than 85% of the total reflection.

In the embodiment, the infrared light can be replaced by other visible or invisible light, such as red visible light, UV invisible light, etc.; the reflective glass can be replaced by other transparent media, such as resin, plastic, precious stone and quartz, etc.; the corresponding incident angle and the threshold which is used to trigger the power-off switch should be adjusted according to the different light and different mediums.

Alternatively, the infrared light can adopt a waveform with a certain frequency, and can also be a pulse infrared light after the modulation and coding, which is different from the outside infrared light, and the corresponding filtering or decoding process will be performed after the reflection and receiving, so as to avoid the received reflected light being influenced by the outside infrared light.

Figure 3:
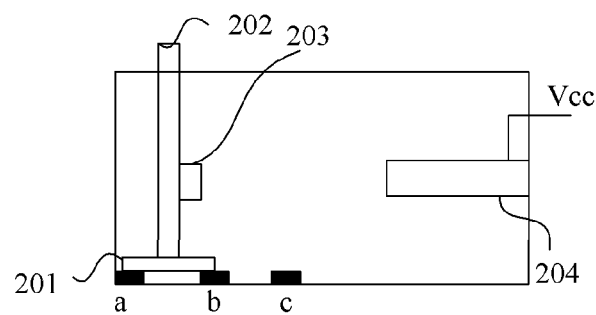
FIG. 3 is a working principle diagram of a disconnection switch circuit of an embodiment of the present document.

As shown in FIG. 3, the working principle of the disconnection switch circuit of the present embodiment is that: the switch contacts, a, b and c, are respectively connected with the circuit board power supply of the mobile phone, the positive electrode of the battery and the ground (the negative electrode of the battery) of the mobile phone circuit; in the normal condition, the shrapnel switch 201 is connected with the contacts a and b, to connect the positive electrode of the battery with the power supply of the mobile phone, and the mobile phone is working normally; When the infrared detects that the mobile phone falls into the water, the power supply module provides a power supply VCC for the electromagnet 204, to enable the electromagnet 204 to adsorb a magnet 203 on the switch button 202; the switch shrapnel 201 is divorced from the contact a and connected with the contacts b and c, the power supply of the mobile phone circuit is disconnected with the positive electrode of the battery, the mobile phone circuit does not work, and there is no input on the VCC of the electromagnet 204. At the same time, the positive and negative electrodes of the battery trigger the short circuit of the battery caused by the switch shrapnel connected with the contracts b and c, to initiate the protection measures in the battery, and the battery has no output. In this case, even if the water goes into the switch which causes the connection between the contacts a and b, because the battery is in a short circuit protection state without any output, there will not be a power-on damage failure of the mobile phone circuit.

Figure 4:
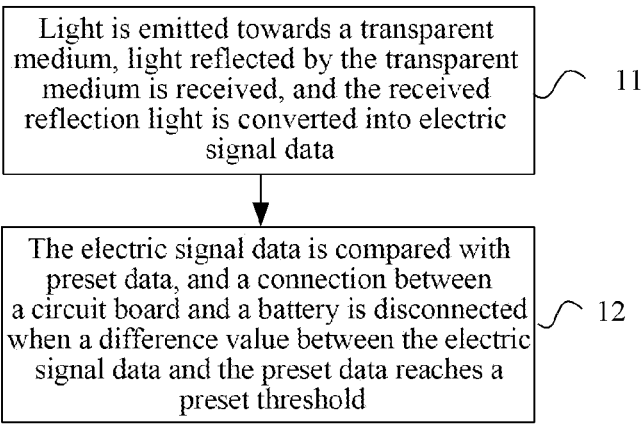
FIG. 4 is a flow chart of an electrical water-resistance method of an embodiment of the present document.

Aiming at the above terminal, the present embodiment further provides an electrical water-resistance method. As shown in FIG. 4, the electrical water-resistance method of the embodiment includes the following steps:

in step 11, light is emitted towards a transparent medium, and light reflected by the transparent medium is received, and the light is converted into electric signal data;

in step 12, the electric signal data are compared with preset data, and a connection between a circuit board and a battery is disconnected when a difference value between the electric signal data and the preset data reaches a preset threshold, wherein, the preset data are electric signal data when the light is totally reflected by the transparent medium, and the preset threshold is preset according to the light and the transparent medium.

In an alternative embodiment, after disconnecting the power supply of the circuit board, it further can include:

connecting to a positive electrode and a negative electrode of the battery.

It can be understood by those skilled in the art that all or part of steps in the above-mentioned method can be fulfilled by programs instructing the relevant hardware components, and the programs can be stored in a computer readable storage medium such as a read only memory, a magnetic disk or an optical disk, etc. Alternatively, all or part of the steps in the above-mentioned embodiments can be implemented with one or more integrated circuits. Accordingly, each module/unit in the above-mentioned embodiments can be implemented in the form of hardware, or in the form of software function module. The present document is not limit to any specific form of the combination of the hardware and software.

The above description is only the alternative embodiments of the present document. Certainly, the present document can further have a variety of other embodiments. Those skilled in the art can make the corresponding modifications and variations according to the present document without departing from the spirit and essence of the present document. And all of these modifications and the variations should be embodied in the protection scope of the appending claims of the present document.

INDUSTRIAL APPLICABILITY

The embodiment of the present document provides a terminal and an electrical water-resistance method, which uses more reliable power-off switch circuit and is able to disconnect the battery output in time when the mobile phone and other terminal products using the lithium battery accidentally fall into the water or are thrown by liquid, to avoid the water damage of the circuit board. Therefore, the present document has very strong industrial practicability.

What is claimed is:

1. A terminal, comprising: a circuit board, a battery and a housing, wherein the battery provides a power source for the circuit board, the housing is provided with a transparent medium used for reflecting light, and the circuit board comprises: a detection module, a control module and a power-off switch, wherein, the detection module emits light towards the transparent medium, and receives the light reflected by the transparent medium, and converts the light into electric signal data and sends the electric signal data to the control module;

the control module, after receiving the electric signal data, compares the electric signal data with preset data and triggers the power-off switch when a difference value between the electric signal data and the preset data reaches a preset threshold, wherein, the preset data are the electric signal data when the light is totally reflected by the transparent medium, and the preset threshold is preset according to the light and the transparent medium; and the power-off switch, after being triggered, disconnects a connection between the circuit board and the battery.

2. The terminal according to claim 1, wherein, the power-off switch, after being triggered, connects to a positive electrode and a negative electrode of the battery.

3. The terminal according to claim 2, wherein, the control module triggers the power-off switch through the following mode:

sending a command of supplying power for the power-off switch to the power-off switch when the difference value between the electric signal data and the preset data reaches the preset threshold.

4. The terminal according to claim 3, further comprising: a power supply module, the power supply module supplies power for the power-off switch after receiving the command of supplying power for the power-off switch; and the power-off switch, after receiving power supply, disconnects the connection between the circuit board and the battery.

5. The terminal according to claim 4, wherein, the power-off switch comprises: an electromagnet and a switch button connected with a switch shrapnel, wherein, the switch shrapnel is connected with the circuit board and the battery;

the power supply module supplies power for the electromagnet after receiving the command of supplying power for the power-off switch; and the electromagnet adsorbs the switch shrapnel after being supplied with power, enables the switch shrapnel to disconnect the connection between the circuit board and the battery, and connects to the positive electrode and the negative electrode of the battery.

6. The terminal according to claim 2, wherein, a refractive index of the transparent medium is larger than a refractive index of water; and the transparent medium comprises any of the following mediums: glass, resin, plastic, precious stone and quartz.

7. The terminal according to claim 1, wherein, the control module triggers the power-off switch through the following mode:

sending a command of supplying power for the power-off switch to the power-off switch when the difference value between the electric signal data and the preset data reaches the preset threshold.

8. The terminal according to claim 7, further comprising: a power supply module, the power supply module supplying power for the power-off switch after receiving the command of supplying power for the power-off switch; and the power-off switch, after receiving power supply, disconnecting the connection between the circuit board and the battery.

9. The terminal according to claim 8, wherein, a refractive index of the transparent medium is larger than a refractive index of water; and the transparent medium comprises any of the following mediums: glass, resin, plastic, precious stone and quartz.

10. The terminal according to claim 8, wherein, the power-off switch comprises: an electromagnet and a switch button connected with a switch shrapnel, wherein, the switch shrapnel is connected with the circuit board and the battery;

the power supply module supplies power for the electromagnet after receiving the command of supplying power for the power-off switch; and the electromagnet adsorbs the switch shrapnel after being supplied with power, enables the switch shrapnel to disconnect the connection between the circuit board and the battery, and connects to the positive electrode and the negative electrode of the battery.

11. The terminal according to claim 10, wherein, a refractive index of the transparent medium is larger than a refractive index of water; and the transparent medium comprises any of the following mediums: glass, resin, plastic, precious stone and quartz.

12. The terminal according to claim 7, wherein, a refractive index of the transparent medium is larger than a refractive index of water; and the transparent medium comprises any of the following mediums: glass, resin, plastic, precious stone and quartz.

13. The terminal according to claim 1, wherein, a refractive index of the transparent medium is larger than a refractive index of water; and the transparent medium comprises any of the following mediums: glass, resin, plastic, precious stone and quartz.

14. An electrical water-resistance method, applied for a terminal described in claim 1, comprising:

emitting light towards a transparent medium set in a housing, and receiving light reflected by the transparent medium, and converting the light into electric signal data; and comparing the electric signal data with preset data, and disconnecting a connection between a circuit board and a battery when a difference value between the electric signal data and the preset data reaches a preset threshold, wherein, the preset data are electric signal data when the light is totally reflected by the transparent medium, and the preset threshold is preset according to the light and the transparent medium.

15. The electrical water-resistance method according to claim 14, wherein, after disconnecting a connection between a circuit board and a battery, the method further comprises:

connecting to a positive electrode and a negative electrode of the battery.

16. The electrical water-resistance method according to claim 14, wherein, the step of disconnecting a connection between a circuit board and a battery comprises:

supplying power for a power-off switch, and the power-off switch disconnecting the connection between the circuit board and the battery after receiving power supply.

17. The electrical water-resistance method according to claim 16, wherein, the power-off switch comprises: an electromagnet and a switch button connected with a switch shrapnel, the switch shrapnel is connected with the circuit board and the battery;

the step of the power-off switch disconnecting the connection between the circuit board and the battery after receiving power supply comprises:

the electromagnet adsorbing the switch shrapnel after being supplied with power, enabling the switch shrapnel to disconnect the connection between the circuit board and the battery, and connecting to the positive electrode and the negative electrode of the battery.

* * * * *